United States Patent
Heuscher et al.

(10) Patent No.: US 7,983,385 B2
(45) Date of Patent: Jul. 19, 2011

(54) FLY-BY SCANNING

(75) Inventors: Dominic J. Heuscher, Aurora, OH (US); Randall P. Luhta, Highland Heights, OH (US); Steven J. Utrup, Willoughby, OH (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 19 days.

(21) Appl. No.: 12/441,916

(22) PCT Filed: Sep. 11, 2007

(86) PCT No.: PCT/US2007/078130
§ 371 (c)(1),
(2), (4) Date: Mar. 19, 2009

(87) PCT Pub. No.: WO2008/042564
PCT Pub. Date: Apr. 10, 2008

(65) Prior Publication Data
US 2009/0238327 A1 Sep. 24, 2009

Related U.S. Application Data

(60) Provisional application No. 60/827,449, filed on Sep. 29, 2006.

(51) Int. Cl.
*A61B 6/00* (2006.01)
(52) U.S. Cl. .................................. 378/11; 378/8; 378/19
(58) Field of Classification Search .................. 378/4, 8, 378/11, 19
See application file for complete search history.

(56) References Cited

U.S. PATENT DOCUMENTS

| | | | |
|---|---|---|---|
| 4,032,789 A * | 6/1977 | Workman | 378/14 |
| 4,191,892 A * | 3/1980 | Huang et al. | 378/14 |
| 4,789,929 A * | 12/1988 | Nishimura et al. | 378/15 |
| 5,170,439 A * | 12/1992 | Zeng et al. | 382/131 |
| 5,224,135 A * | 6/1993 | Toki | 378/4 |
| 5,463,666 A * | 10/1995 | Eberhard et al. | 378/4 |
| 5,625,661 A | 4/1997 | Oikawa | |
| 5,706,325 A * | 1/1998 | Hu | 378/4 |
| 5,864,597 A | 1/1999 | Kobayashi | |

(Continued)

FOREIGN PATENT DOCUMENTS

EP  1099409 A2  5/2001

(Continued)

OTHER PUBLICATIONS

Pack, J. D., et al.; Investigation of saddle trajectories for cardiac CT imaging in cone-beam geometry; 2004; Phys. Med. Biol.; 49:2317-2336.

*Primary Examiner* — Edward J Glick
*Assistant Examiner* — Alexander H Taningco

(57) ABSTRACT

A computed tomography system (100) includes an x-ray source (112) that rotates about an examination region (108) and translates along a longitudinal axis (120). The x-ray source (112) remains at a first location on the longitudinal axis (120) while rotating about the examination region (108), accelerates to a scanning speed and performs a fly-by scan of a region of interest (220) in which at least one hundred and eighty degrees plus a fan angle of data is acquired. At least one detector (124) detects x-rays radiated by the x-ray source (112) that traverses the examination region (108) and generates signals indicative thereof. A reconstructor (132) reconstructs the signals to generate volumetric image data.

25 Claims, 6 Drawing Sheets

U.S. PATENT DOCUMENTS

| | | | |
|---|---|---|---|
| 6,014,419 A * | 1/2000 | Hu | 378/4 |
| 6,256,369 B1 | 7/2001 | Lai | |
| 6,430,253 B1 * | 8/2002 | Oikawa | 378/15 |
| 6,539,074 B1 * | 3/2003 | Yavuz et al. | 378/4 |
| 6,560,308 B1 * | 5/2003 | Zmora | 378/4 |
| 2001/0048731 A1 * | 12/2001 | Nakamura et al. | 378/4 |
| 2002/0025018 A1 * | 2/2002 | Takagi et al. | 378/8 |
| 2002/0037068 A1 * | 3/2002 | Oikawa | 378/15 |
| 2002/0131544 A1 * | 9/2002 | Aradate et al. | 378/4 |
| 2004/0081270 A1 * | 4/2004 | Heuscher | 378/4 |
| 2005/0074085 A1 * | 4/2005 | Hsieh et al. | 378/4 |
| 2005/0100126 A1 | 5/2005 | Mistretta et al. | |
| 2005/0152494 A1 * | 7/2005 | Katsevich | 378/62 |

FOREIGN PATENT DOCUMENTS

| | | |
|---|---|---|
| EP | 1457156 A1 | 9/2004 |
| WO | WO 2004075115 A1 * | 9/2004 |

* cited by examiner

FLY-BY SCANNING

CROSS REFERENCE TO RELATED APPLICATIONS

This application claims the benefit of U.S. provisional application Ser. No. 60/827,449 filed Sep. 29, 2006, which is incorporated herein by reference.

DESCRIPTION

The present application generally relates to imaging systems. In particular, it relates to computed tomography (CT) and, more particularly, to data acquisition.

Conventional cone beam CT systems have included multi-slice detectors, which enable such systems to scan larger regions/volumes of interest in shorter periods of time relative to their single-slice system predecessors. Such scanning can be leveraged to quickly scan whole or large portions of organs and improve temporal resolution.

By way of example, with cardiac CT it is often desirable to scan the heart during a quiet or resting phase of the heart cycle. Using prospective gating, electrical activity of the heart is concurrently monitored during a scanning procedure. Upon sensing a known landmark within the electrical activity, such as an R wave, the x-ray source is turned on for a data acquisition period in which the heart is scanned during the desired cardiac phase.

However, conventional cone beam CT axial scans following a circular orbit are limited in that they do not acquire complete sampling for reconstruction (or fail to adequately sample portions of the scanned region/volume of interest). In general, at least 180 degrees plus a fan angle (or about 240 degrees) of data is needed for a 180 degree reconstruction. As a result of incomplete sampling, the reconstructed data will include cone beam artifact.

Two approaches for acquiring complete data with cone beam CT are discussed next. One approach is to move the patient through the examination region via a patient support or couch while the x-ray source rotates around the examination region. However, increases in rotating gantry speeds and the number of detector rows require relatively greater couch speeds, which complicate the mechanical implementation of couch motion and may not be well-tolerated by some patients.

Another approach is to sweep the focal spot through a saddle orbit. With this approach, the focal spot is cyclically and continuously swept along the z-axis direction at a frequency of two (2) cycles per gantry rotation (three hundred and sixty (360) degrees). Unfortunately, this results in a relatively larger source trajectory, which may require a larger detector. In addition, the saddle orbit requires relatively rapid acceleration and deceleration of the focal spot.

Aspects of the present application address the above-referenced matters and others.

According to one aspect, a computed tomography system includes an x-ray source that rotates about an examination region and translates along a longitudinal axis. The x-ray source remains at a first location on the longitudinal axis while rotating about the examination region, accelerates to a scanning speed, and performs a fly-by scan of a region of interest in which at least one hundred and eighty degrees plus a fan angle of data is acquired. At least one detector detects x-rays radiated by the x-ray source that traverse the examination region and generates signals indicative thereof. A reconstructor that reconstructs the signals to generate volumetric image data.

According to another aspect, a computed tomography system includes an x-ray source that rotates about an examination region and translates along a longitudinal axis. The motion of the x-ray source and emission of x-rays thereby are coordinated with and gated by a motion state of anatomy disposed within the examination region. At least one detector disposed opposite from the x-ray source on a different side of the examination region detects x-rays radiated by the x-ray source that traverse the examination region.

According to another aspect, a computed tomography method includes maintaining an x-ray source at a static longitudinal location on a z-axis while it rotates around an examination region. The x-ray source is moved in a direction along the z-axis during a desired motion state of anatomy disposed within the examination region upon receiving a trigger signal indicative of the desired motion state and is activated to irradiate anatomy disposed within the examination region while translating during the desired motion state of the anatomy.

According to another aspect, a computed tomography system performs fly-by scans gated by periodic motion of an organ being scanned.

The invention may take form in various components and arrangements of components, and in various steps and arrangements of steps. The drawings are only for purposes of illustrating the preferred embodiments and are not to be construed as limiting the invention.

Figure 3:
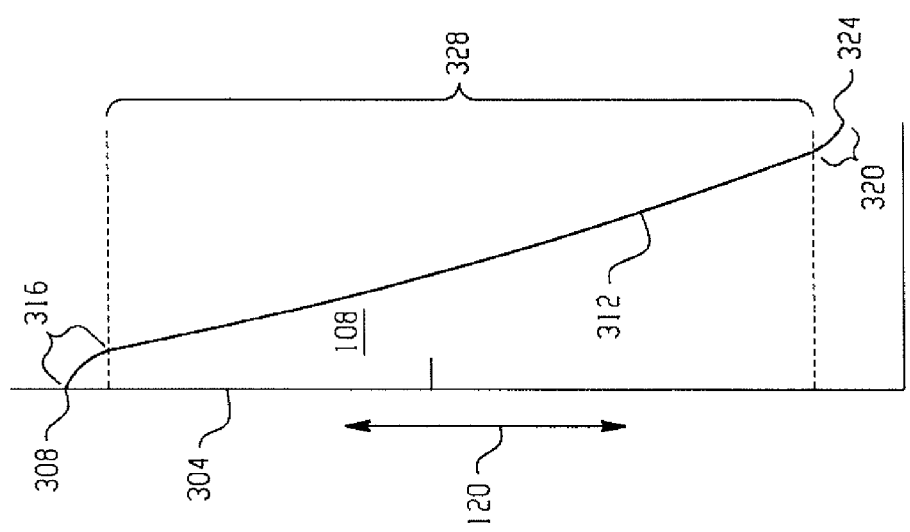

FIG. 3 graphically illustrates exemplary x-ray tube/source motion as a function of time.

Figure 4:
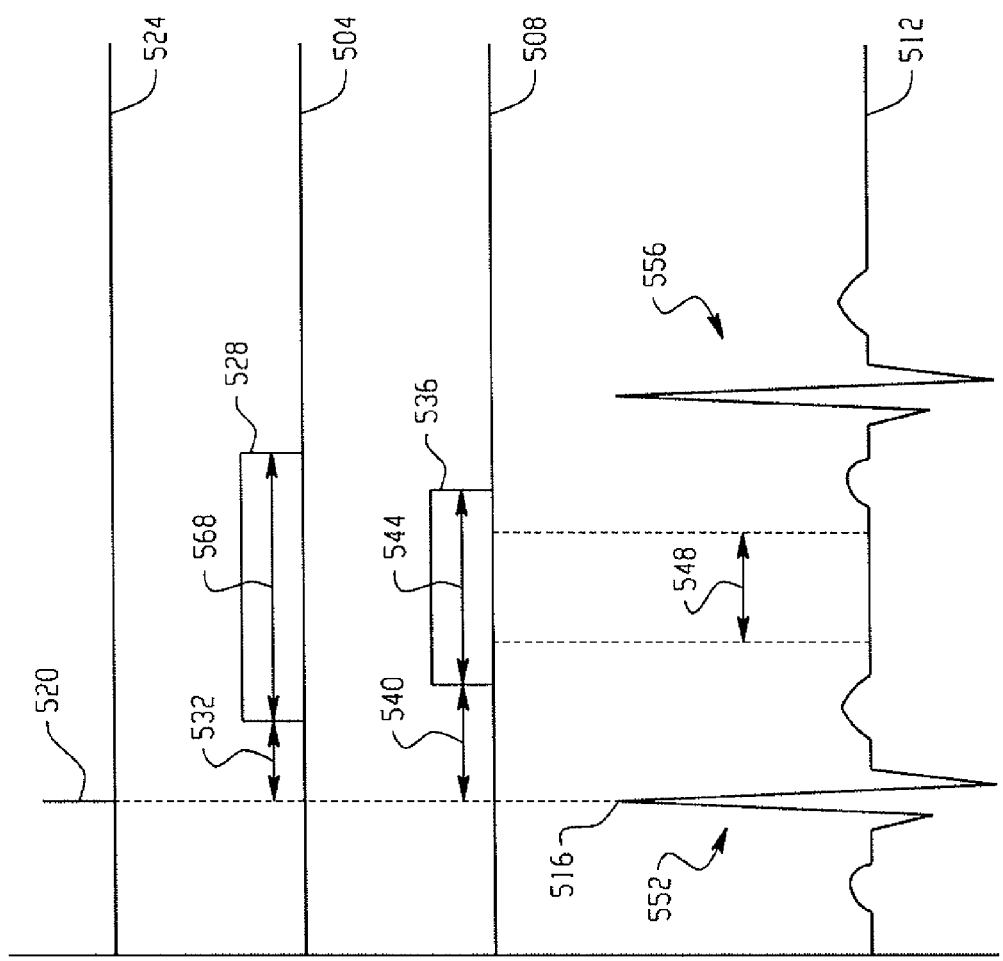

FIG. 4 illustrates exemplary fly by scanning timing diagrams.

Figure 5:
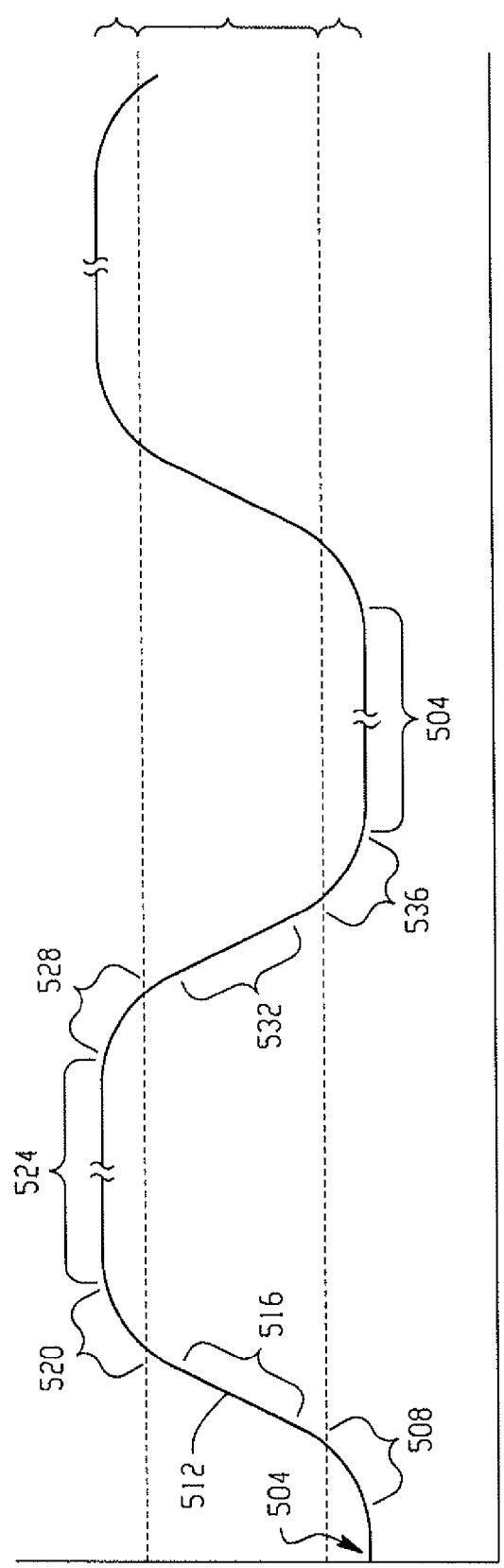

FIG. 5 graphically illustrates exemplary x-ray tube/source motion for multiple fly-by scans.

Figure 6:
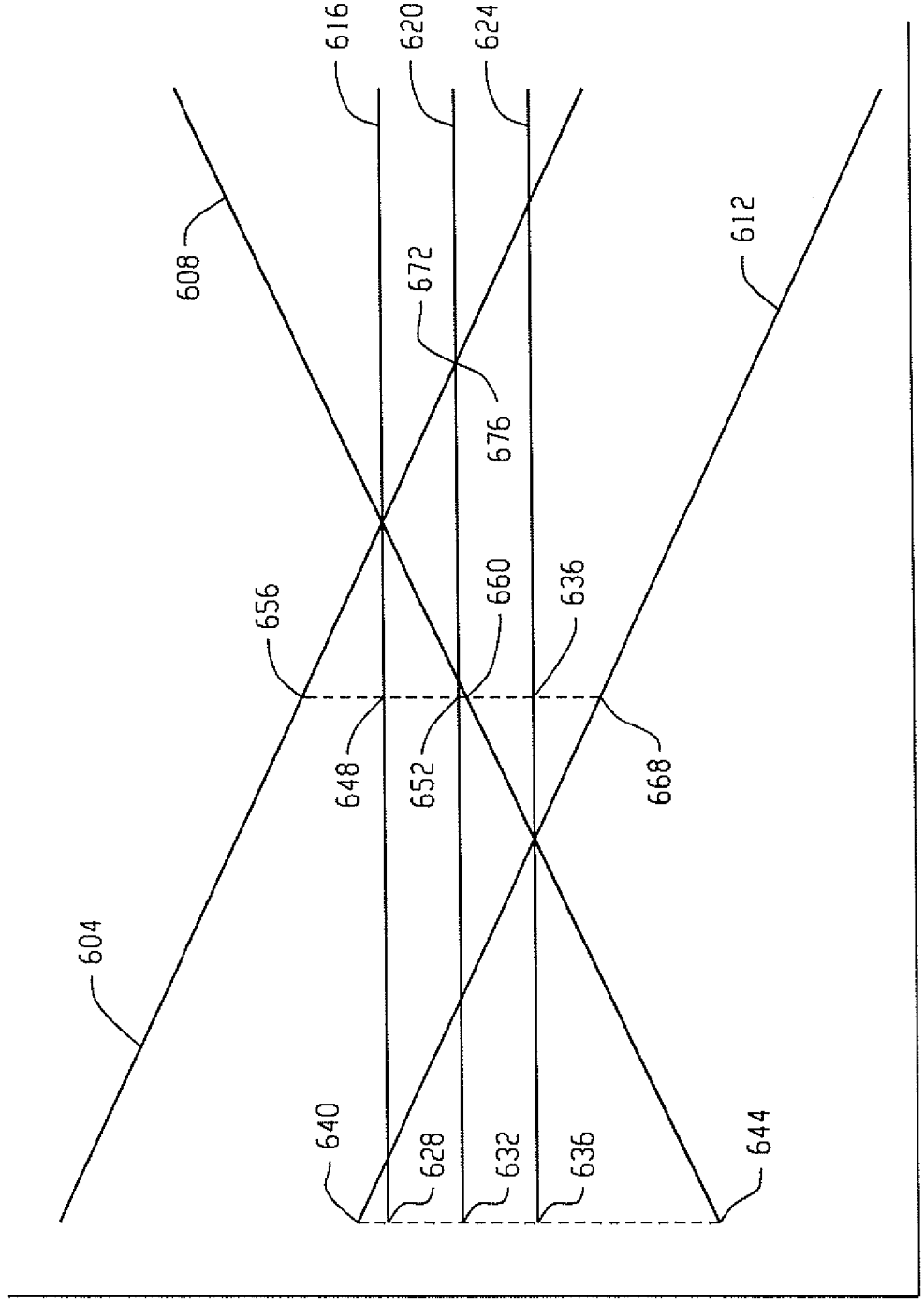

FIG. 6 illustrates an exemplary technique for generating data from reconstructed data.

Figure 1:
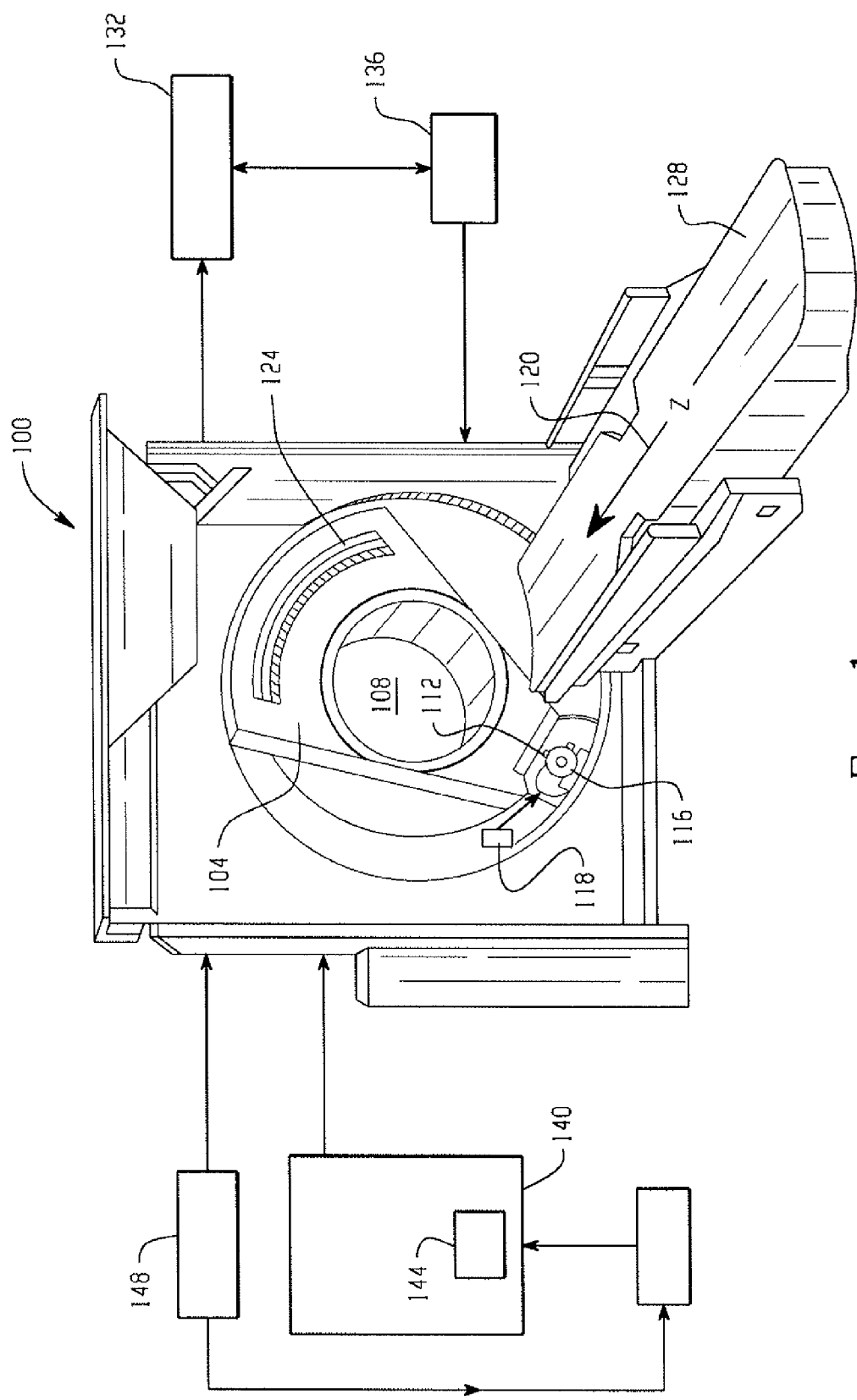
FIG. 1 illustrates an exemplary imaging system.
Figure 7:
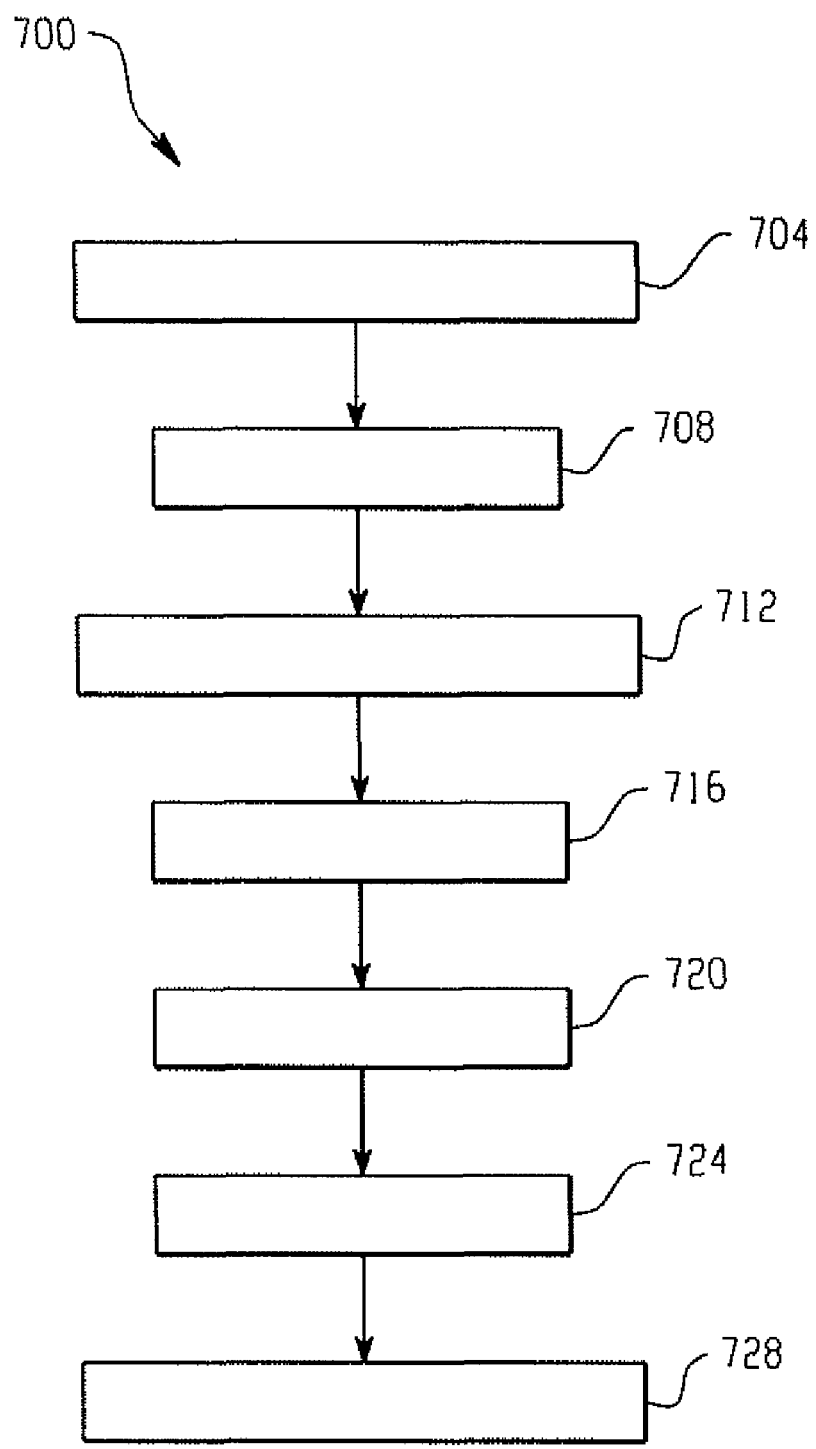

FIG. 7 illustrates an exemplary method for scanning with the system of FIG. 1.

With reference to FIG. 1, a CT imaging system 100 includes a rotating gantry portion 104 that rotates about an examination region 108. The rotating gantry portion 104 supports an x-ray source 112 that radiates an x-ray beam that is collimated to have a generally conical geometry. In the illustrated embodiment, the x-ray source 112 originates from an x-ray tube 116. A drive mechanism 118 moves the x-ray tube 116 and, thus, the x-source 112, longitudinally along a z-axis 120. In one implementation, the motion of the x-ray tube 116 and emission of radiation by the x-ray source 112 are coordinated with motion of an object such as anatomy disposed within the examination region 108 or flow of a contrast agent or the like through the object or anatomy disposed within the examination region 108. As described below, such coordination can be used with fly-by scanning, for example, wherein the object is scanned during a desired motion state or flow of the agent is traced through the object.

The rotating gantry portion 104 also supports an x-ray sensitive detector array 124, which is disposed about the rotating gantry portion 104 to subtend an angular arc opposite the x-ray source 112. The detector array 124 includes a multi-slice detector having a plurality of detector elements extending in the axial and transverse directions. Each detector element detects radiation emitted by the x-ray source 112 that traverses the examination region 108 and generates corresponding output signals or projection data indicative of the detected radiation. As depicted, the detector array 124 is arranged in a third generation configuration. However, other configurations such as fourth generation are also contemplated herein.

The CT imaging system 100 further includes a couch or patient support 128 that supports a human or object within the examination region 108. The support 128 is movable, which enables an operator or the system to suitably position the subject within the examination region 108 for scanning. Once suitably positioned within the examination region 108, the patient support 128 generally remains stationary during scanning. However, the patient support 128 moves during scanning when performing scout or pilot or otherwise, if desired.

The projection data generated by the detector array 124 is conveyed to a reconstructor 132, which reconstructs the projections and generates volumetric image data therefrom. The image data is processed to generate one or more images of the scanned region of interest or a subset thereof.

An operator console 136 facilitates user interaction with the scanner 100. Software applications executed by the operator console 136 allow the user to configure and/or control operation of the scanner 100. For instance, the user can interact with the operator console 136 to select scan protocols, and initiate, pause and terminate scanning. The console 136 also allows the user to view images, manipulate the data, measure various characteristics of the data (e.g., CT number, noise, etc.), etc.

The illustrated embodiment is configured for scanning applications involving periodically moving anatomy and tracer agents. An optional physiological monitor 140 monitors cardiac, respiratory, or other motion of the object. In this example, the monitor 140 includes an electrocardiogram (ECG) or other device 144 that monitors the electrical activity of the heart. This information is used to trigger one or more fly-by scans or to synchronize fly-by scanning with the heart electrical activity. An optional injector 148 or the like is used to introduce agents such as contrast into the subject. Likewise, the introduction of the agent is used to trigger one or more fly-by scans.

Figure 2:
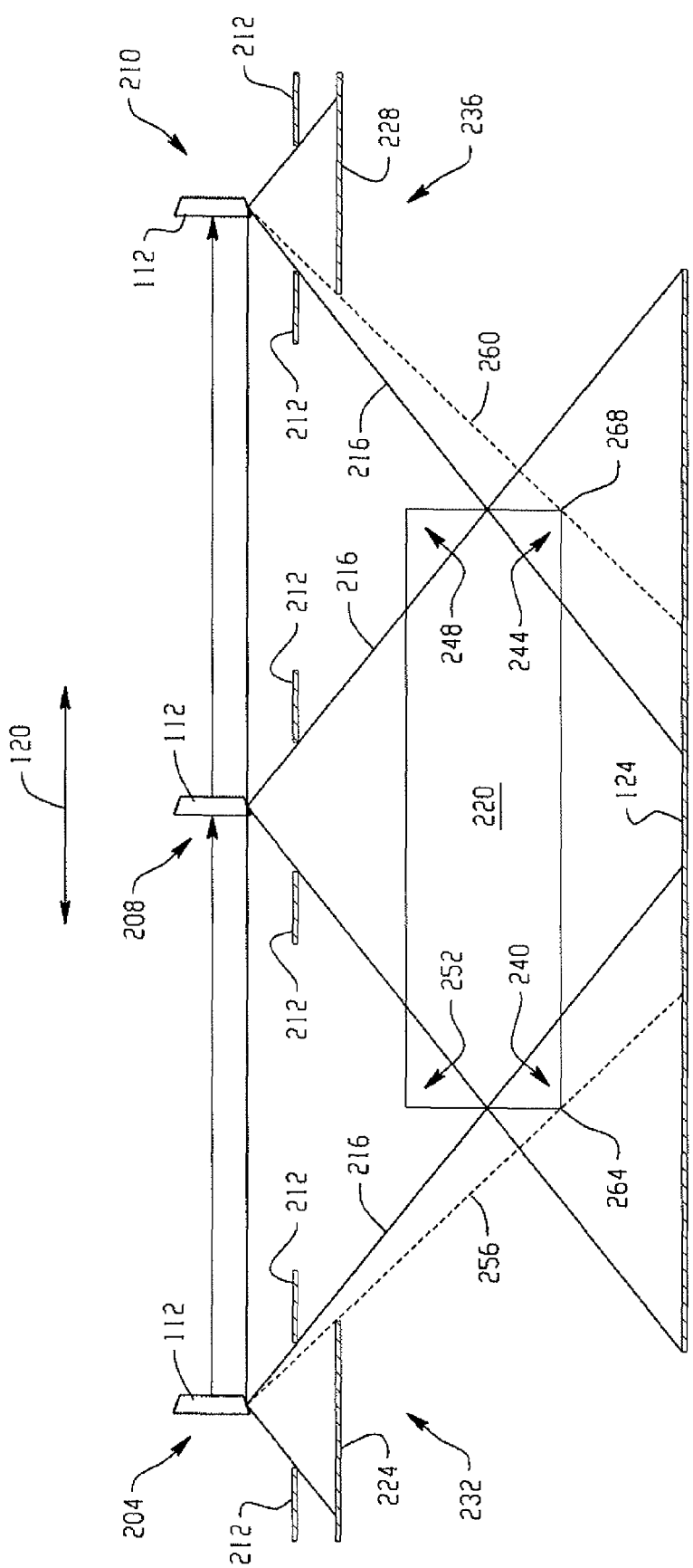
FIG. 2 illustrates exemplary motion of an x-ray source.

FIG. 2 illustrates exemplary motion of the x-ray source 112 along the z-axis 120 during a fly-by scan and corresponding x-ray beam geometry. In this example, the x-ray source 112 is shown moving from a first position 204, through a second position 208, to a third position 210. While translating between the first and third positions 204 and 210, the x-ray source 112 rotates around the examination region 108 and emits x-rays. The x-ray source 112 may also move from the third position 210, through the second position 208, to the first position 204, for example, when performing the initial or a subsequent scan. Physical movement of the x-ray tube 116 and the x-ray source 112 extends outside of a region defined by the first and third positions 204 and 210 to allow for accelerating or ramping up the x-ray tube 116 to a suitable speed prior to a scan and decelerating or ramping down the x-ray tube 116 after the scan.

During a fly-by scan, the x-ray tube 116 remains at the location outside of the position 204 (or 210) along the z-axis while rotating. The x-ray tube 116 then ramps up to a suitable scanning speed and moves in the direction of the position 210 (or 204). Upon reaching the initial scanning position 204 (or 210), x-rays are emitted for a sampling period in which complete sampling for a 180 degree reconstruction for each voxel throughout the volume is performed. It is to be appreciated that during a fly-by scan, the x-ray tube 116 can move at a constant or a variable speed. Upon reaching the position 210 (or 204), x-rays are turned off and the x-ray tube 116 decelerates to another location outside of the positions 210 (or 204).

The geometry of the cone beam is defined by collimators 212. The collimators 212 move with a fixed collimation in coordination with the movement of the x-ray source 112. Optional stationary collimators 224 and 228 are located at first and second regions 232 and 236, respectively, along the z-axis 120. The stationary collimators 224 and 228 filter or block portions of the x-ray beam as the x-ray source 112 approaches the first and third positions 204 and 210. The stationary collimators 224 and 228 are configured to collimate the x-ray beam 216 so that the x-ray beam 216 irradiates sub-regions 240, 244, 248, and 252 of the region of interest 220 as the x-ray source 112 moves between the first and third positions 204 and 210 while rotating. This configuration provides complete sampling. Radiation exposure to the patient by x-rays traversing paths outside of the region of interest 220 is reduced by blocking portions of the x-ray beam 216 by the collimators 224 and 228 so that outer projections 256 and 260 of the x-ray beam 216 illuminating the detector array 124 respectively cross corners 264 and 268 of the region of interest 220.

FIG. 3 graphically illustrates an exemplary motion of the x-ray tube 116 along the z-axis 120 as a function of time. An axis 304 represents motion along the z-axis 120. In this example, a position 308 on a path 312 represents an initial z-axis position of an x-ray tube 120 as a function of time. This position can be on either side of the z-axis 120. A first portion 316 of the path 312 represents a region in which the x-ray tube 116 accelerates to a suitable velocity. X-rays typically are not emitted as the x-ray tube 116 travels through the portion 316. A second portion 320 of the path 312 represents a region in which the x-ray tube 116 decelerates to a position 324 on the path 312. Likewise, x-rays typically are not generated as the x-ray tube 116 travels through the portion 320. A third portion 328 of the path 312 represents a region in which fly-by scans are performed. This region may be linear or non-linear. During the portion 328, complete sampling is acquired for the region of interest 220 (shown in FIG. 2).

FIG. 4 illustrates a timing diagram 504 for x-ray tube motion and a timing diagram 508 for emission of radiation, both coordinated with an ECG signal 512. As depicted, an R-wave 516 within the ECG signal 512 provides a trigger 520 (shown in a trigger timing diagram 524) that invokes x-ray tube motion during an x-ray tube motion window 528 after a first delay 532 and emission of x-rays during a scanning window 536 after a second delay 540. It is to be appreciated that other waves within the ECG signal 512 can alternatively be used as the trigger 520.

The location of the scanning window 536, its width 544, and the delay 532 typically are defined based on a desired cardiac phase. For instance, in the illustrated example the scanning window 536, the width 544, and the delay 532 are defined to scan a quiet phase 548, or low motion phase, within a heart cycle based on the ECG signal 512. During a heart contraction period, the device 152 measures electrical activity representative thereof, including the R wave 516. Since the heart generally beats with periodicity, the R wave 512 or any of the other waves can be used as a reference to the quiet phase 548 and a subsequent heart cycle.

As such, the scanning window 536 and the width 544 can be defined around the quiet phase 548, with delay 540 defined from the R wave 516. Multiple heart cycles can be observed prior to determining such parameters. The width 544 is defined so that at least 180 degrees plus a fan angle is acquired for a 180 degree reconstruction. A larger width 544 can be used to scan a relatively greater extent, wherein a suitable amount of data is selected therefrom for reconstructing different portions of the scanned object. Typically, the data closer to the ends of the window 544 and generally further from the quiet region include more motion.

The location of the x-ray tube motion window 528, its width 568, and the first delay 532 are defined based on the scanning window 536 and R wave 516 so that the x-ray tube 116 has enough time to ramp up to speed prior to a fly-by scan, maintain a suitable speed during the fly-by scan, and ramp down after the fly-by scan in time for another fly-by scan, if desired.

By way of example, with a gantry rotational speed of about twenty-seven hundreths (0.27) of a second per rotation, a pitch factor of one and a half (1.5), source collimation set for one hundred and sixty (160) millimeters (mm), and two-hundred and fifty-six (256) detector elements in the z-axis direction, the width 540 is about thirty-six hundreths (0.36) of a second, which results in scan coverage of about one hundred and sixty (160) mm over four-hundred and eighty (480) degrees, or about one and a third (1.33) revolutions. With these settings, the oscillation of the x-ray tube 116 is about three hundred and fifty (350) mm at about one and two hundreths (1.02) Hz and the g-force is about seventy-three hundreths (0.73) g. A sliding window with a width of about eighteen hundreths (0.18) of a second is used to select a suitable one hundred and eighty degrees plus a fan angle of data from the four-hundred and eighty (480) degrees of data for reconstruction of each slice. It is to be appreciated that this example is provided for explanatory purposes and that various other parameter configurations are also contemplated herein.

FIG. 5 graphically illustrates movement of the x-ray source 112 for multiple fly-by scans. The x-ray tube 116 remains at an initial position 504 until a biological event of interest or trigger signal is received while the rotating gantry portion 104 and, hence, the x-ray tube 116 and source 112 rotates. The amount of time the x-ray tube 116 is at this position depends on various factors such as the frequency of the heart cycle of the patient, the number of cycles observed prior to scanning, etc. When the event is received, the x-ray tube 116 accelerates through a first portion 508 of a path 512. For at least a sub-portion of a second portion 516 of the path 512, x-ray are turned on during a desired state of the anatomy for a fly-by scan of the anatomy. After scanning, the x-ray tube 116 decelerates within a third portion 520 of the path 512 and remains at a fourth portion 524 of the path 512.

Wait times may vary from fly-by scan to fly-by scan and again depend on factors such as the frequency of the heart cycle of the patient, the number of cycles observed prior to performing another fly-by scan, etc. Upon receiving a subsequent event of interest, the x-ray tube 116 accelerates in an opposite z-axis direction through a fifth portion 528 of a path 512, and x-ray are turned on during a sixth portion 532 of the path 512 for at least a sub-portion of the sixth portion 532. The x-ray tube 116 then decelerates within a seventh portion 536 of the path 512 and remains at a eighth portion 540 of the path 512 for a next event of interest. This is repeated for each fly-by scan.

In general, one fly-by scan provides enough data to reconstruct the desired phase. However, several instances exist in which more than one fly-by scan is desirable. For example, multiple phases of the heart can be imaged by scanning a different phase with each fly-by of the x-ray tube 116. In another instance, a subsequent fly-by can be used to repeat a scan deemed unacceptable or that was aborted. For example, an arrhythmia may trigger the x-ray tube 220 to move and irradiate the region of interest. In yet such an instance, x-ray emission can be halted since the arrhythmia represents an anomaly in the rhythm of the heart cycle. Another fly-by scan can then be invoked to scan the same cardiac phase. In another example, data from multiple fly-by scans are combined to improve temporal resolution. In still another example, an object can be scanned at different times in order to follow an agent as it moves through the subject. For example, a series of sequential fly-by scans of the same object can be performed, wherein each fly-by scan images the state or location of the agent in the object at a particular moment in time. The resulting data can be used to trace the flow of agent through the object.

FIG. 6 illustrates an approach for generating phase corrected image data. As depicted, image data 604, 608, and 612 for different fly-by scans each have phase differences between slices as a function of slice position along the z-axis. As a result, each slice is associated with a different phase. New data 616, 620, and 624 is generated from the data 604, 608, and 612 to reduce the phase difference between slices for each fly-by scan. In this example, an interpolation technique is utilized to create the phase corrected data 616, 620, and 624. For example, new data 628, 632, and 636 are created via interpolation using data 640 and 644. New data 648 and 652 are created via interpolation using data 656 and 660, and new data 636 is created via interpolation using data 660 and 668. In another example, data 672 is used as new data 676 since the data 672 and the image data 676 have the same phase. U)sing this technique, one or more slices within each new data set 628, 632, and 636 have the same phase. In this example, data from three (3) fly-by scans is illustrated. However, it is to be appreciated that reconstructed image data from N fly-by scans can be used to generate an arbitrary number of phase corrected data sets. In addition, various interpolation techniques such as, but not limited to, linear, polynomial, and spline interpolation, using two or more data points from the reconstructed fly-by scan data, are contemplated herein.

FIG. 7 illustrates a method 700 for scanning with the system 100. At reference numeral 704, the x-ray source 112 is at an initial location on the z-axis 120 while the rotating gantry 104 rotates around the examination region 108. At 708, an event of interest such as a trigger is received. At 712, the x-ray source 112 accelerates to a suitable speed. At 716, the x-ray source 112 is activated to emit radiation. At 720, radiation that traverses the region of interest is detected by the detector array 124. At 724, the x-ray source 112 ceases to emit x-rays. At 728, the x-ray tube 116 decelerates to another position.

Other variations are now presented.

In another embodiment, the x-ray tube 116 continuously oscillates back and forth along the z-axis 120. With this embodiment, fly-by scans are automatically invoked through synchronization with the heart electrical activity.

In another embodiment, a plurality of fly-by scans are arbitrarily performed, and retrospective gating is used to subsequently select suitable data for a 180 degree reconstruction based on recorded heart electrical activity.

In one implementation, a spring based or other mechanism is used to move the x-ray tube 116 back and forth along the z-axis.

In another implementation, the x-ray tube 116 is mounted to and moves with a linear bearing. One or more optional counter weights that move in coordination with the x-ray tube 116 are used to mitigate gantry wobble or other deleterious affects resulting from moving the tube 116, if desired.

A one hundred (100) kilowatt (KW) or other power rated x-ray tube is used with the system 100.

The invention has been described with reference to the preferred embodiments. Modifications and alterations may occur to others upon reading and understanding the preceding detailed description. It is intended that the invention be con-

Having thus described the preferred embodiments, the invention is now claimed to be:

1. A computed tomography system, comprising:
an x-ray source that rotates about an examination region and translates along a longitudinal axis, wherein the x-ray source remains at a first location on the longitudinal axis while rotating about the examination region, accelerates along the longitudinal axis to a scanning speed, and performs a fly-by scan of a region of interest in which the x-ray source concurrently rotates about the examination region and translates along the longitudinal axis while at least one hundred and eighty degrees plus a fan angle of data is acquired;
at least one detector that detects x-rays radiated by the x-ray source that traverse the examination region and generates signals indicative thereof; and
a reconstructor that reconstructs the signals to generate volumetric image data.

2. The system of claim 1, wherein x-rays are turned off after acquiring the data and the x-ray source stops at a second location on the longitudinal axis.

3. The system of claim 2, wherein the x-ray source remains at the second location while rotating about the examination region, accelerates to the scanning speed, and performs another fly-by scan of the region of interest.

4. The system of claim 1, wherein the x-rays are turned off after acquiring the data and the x-ray source reverses directions and accelerates in an opposite direction along the longitudinal axis.

5. The system of claim 4, wherein the x-ray source performs a subsequent fly-by scan of the region of interest while moving in the opposite direction.

6. The system of claim 1, wherein the x-ray source oscillates along the longitudinal axis and is synchronized with motion of an object in the examination region.

7. The system of claim 1, wherein the x-ray source remains at the location until a trigger signal is received.

8. The system of claim 7, wherein the trigger signal is an ECG signal.

9. The system of claim 1, wherein the x-ray source performs the fly-by scan of a cardiac phase.

10. The system of claim 1, wherein the x-ray source performs multiple fly-by scans during different cardiac phases.

11. The system of claim 1, wherein the x-ray source performs multiple fly-by scans at different times during the same cardiac phase.

12. The system of claim 1, wherein image data from multiple fly-by scans respectively with phase difference between slices is used to generate new image data without phase differences between slices.

13. The system of claim 12, wherein a new slice is generated by interpolating the same slice in the image data from the multiple fly-by scans.

14. The system of claim 1, further including stationary collimators that reduce patient exposure from x-rays traversing paths outside of a region of interest within the examination region.

15. The system of claim 1, further including an injector, wherein the motion of the x-ray source and emission of x-rays therefrom is gated via introduction of an agent into the object by the injector.

16. A computed tomography system, comprising:
an x-ray source that concurrently rotates about an examination region and translates along a longitudinal axis while emitting radiation during a scan wherein the motion of the x-ray source and emission of x-rays thereby are coordinated with and gated by a motion state of anatomy disposed within the examination region;
a rotating gantry portion that supports the x-ray source and that rotates about the examination region, wherein the x-ray source translates along the rotating gantry portion along the longitudinal axis;
a drive mechanism that moves the x-ray source along the longitudinal axis, wherein the x-ray source waits at a z-axis location while rotating until a desired motion state of the anatomy, which triggers a fly-by scan in which the x-ray source accelerates along rotating gantry portion along the longitudinal axis, to a suitable speed and the x-ray source is activated to scan the anatomy during the desired motion state; and
at least one detector that detects x-rays radiated by the x-ray source that traverses the examination region.

17. The system of claim 16, wherein image data from multiple scans, each having phase, differences, is used to generate image data without phase differences.

18. The system of claim 16, further including an ECG device that gates the x-ray source to move and scan a desired phase of the heart.

19. A method, comprising:
causing, via a computed tomography system, an x-ray source to rotate about an examination region;
causing, via the computed tomography system, the x-ray source to translate along a longitudinal axis, wherein the x-ray source remains at a first location on the longitudinal axis while rotating about the examination region, accelerates along the longitudinal axis to a scanning speed, and performs a fly-by scan of a region of interest in which the x-ray source concurrently rotates about the examination region and translates along the longitudinal axis while at least one hundred and eighty degrees plus a fan angle of data is acquired.

20. The method of claim 19, where at least one detector detects x-rays radiated by the x-ray source that traverse the examination region and generates signals indicative thereof.

21. The method of claim 20, comprising:
causing, via the computed tomography system, reconstruction of the signals to generate volumetric image data.

22. The method of claim 21, wherein x-rays are turned off after acquiring the data and the x-ray source stops at a second location on the longitudinal axis and wherein the x-ray source remains at the second location while rotating about the examination region, accelerates to the scanning speed, and performs another fly-by scan of the region of interest.

23. The method of claim 21, wherein the x-rays are turned off after acquiring the data and the x-ray source reverses directions and accelerates in an opposite direction along the longitudinal axis and wherein the x-ray source performs a subsequent fly-by scan of the region of interest while moving in the opposite direction.

24. The method of claim 21, wherein the x-ray source remains at the location until an ECG trigger signal is received.

25. The method of claim 21, wherein image data from multiple fly-by scans respectively with phase difference between slices is used to generate new image data without phase differences between slices and wherein a new slice is generated by interpolating the same slice in the image data from the multiple fly-by scans.

* * * * *